United States Patent [19]

Von Esch et al.

[11] 4,272,528

[45] Jun. 9, 1981

[54] PHOSPHONOACETYL AMINOACIDS

[75] Inventors: Anne M. Von Esch, North Chicago; Alford M. Thomas, Wadsworth; John S. Fairgrieve, Lake Villa; John H. Seely, Lake Forest, all of Ill.

[73] Assignee: Abbott Laboratories, North Chicago, Ill.

[21] Appl. No.: 178,191

[22] Filed: Aug. 14, 1980

[51] Int. Cl.³ .................... A61K 31/60; C07F 9/38
[52] U.S. Cl. ................................. 424/211; 260/502.5
[58] Field of Search ...................... 260/502.5; 424/211

[56] References Cited

U.S. PATENT DOCUMENTS

| 3,767,795 | 10/1973 | Schleicher et al. | 424/212 |
| 4,087,522 | 5/1978 | Von Esch | 424/211 |
| 4,138,432 | 2/1979 | Von Esch | 260/502.5 |
| 4,215,070 | 7/1980 | Schultz et al. | 260/502.5 |

OTHER PUBLICATIONS

Swyryd et al., "J. Biol. Chem.", 249, No. 21, pp. 6945–6950, 1974.

Abstracts of 176th ACS Ntl. Meeting; ISBN 8412-04-47-0, Medicinal Section, No. 27.

Primary Examiner—Joseph E. Evans
Attorney, Agent, or Firm—Paul D. Burgauer; Robert L. Niblack

[57] ABSTRACT

Certain phosphonoacetyl aminoacids have been found to be useful antiviral agents suitable to combat herpes virus infection of various types.

21 Claims, No Drawings

PHOSPHONOACETYL AMINOACIDS

DETAILED DESCRIPTION OF THE INVENTION

From U.S. Pat. No. 3,767,795 it is known that phosphonoacetic acid (PAA) is a useful tool to combat herpes infections of various types. Upon topical applications, PAA frequently causes skin irritations and also some evidence of PAA-resistant virus has been reported. The search for PAA derivatives which overcome these and other detriments has thus continued and new compounds with equal to better activity and diminished side effects have now been discovered.

According to the present invention, there is provided a new group of antiviral PAA derivatives which are represented by the formula

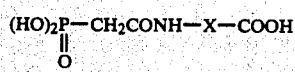

wherein X stands for $>$CHCH$_3$, —CH$_2$—, —CH$_2$CH$_2$—, $>$CHCH$_2$CH(CH$_3$)$_2$, $>$CHCH$_2$CONH$_2$ or

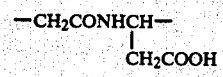

and the nontoxic salts thereof. These compounds can be expressed also as PAA-Ala, PAA-Gly, PAA-β-Ala, PAA-Leu, PAA-Asn or PAA-Gly-Asp, using standard aminoacid abbreviations. The new compounds are considerably less acidic and therefore produce much less skin irritations. Likewise, as derivatives of aminoacids, these compounds show better skin penetration, more rapid secretion and better lipophilicity.

In a general embodiment, the above compounds are made by condensing P,P-diphenyl-PAA with the benzyl ester of alanine, glycine, leucine, asparagine or β-alanine using a catalyzed carbodiimide reaction in the customary fashion of peptide synthesis. In addition to the protected phosphonoacetic acid and amino acid the reaction medium consists of an inert solvent, an alkaline agent, N,N-dicyclohexylcarbodiimide and a catalyst selected from N-hydroxysuccinimide, 1-hydroxybenztriazole or similar agent. The condensation product is deblocked over a noble metal catalyst. When the desired end product is PAA-Gly-Asp, a suitable method consists in reacting an active ester of dimethyl-PAA or preferably the dibenzyl-PAA with Gly-Asp(Bzl)$_2$ in the above manner, debenzylating the condensation product in the previously mentioned fashion, followed by removing the methyl groups in the PAA moiety in known manner.

The current invention is more particularly described by reference to the following examples which, however, are not intended to limit the invention in any respect. All rotations, [α]$_D$, are recorded at the sodium D-line.

EXAMPLE 1

Equimolar amounts of P,P-diphenyl-PAA, N-hydroxysuccinimide and glycine benzyl ester were dissolved in N,N-dimethylformamide (DMF). The solution was stirred at −20° C. when equimolar amounts of triethylamine and N,N'-dicyclohexylcarbodiimide dissolved in a small volume of DMF were added. After 2 hours at −20° C., stirring was continued 14 hours at room temperature, before filtration of the mixture and evaporation of the filtrate in vacuo. The residual oil was dissolved in ethyl acetate, washed twice with 5% aqueous sodium bicarbonate, twice with 1.0 N hydrochloric acid and once with saturated aqueous sodium chloride. The organic layer was then dried over anhydrous sodium sulfate, evaporated in vacuo, leaving again an oil in a yield of 97% of theory, calculated on the basis of the expected P,P-diphenylphosphonoacetylglycine benzyl ester. This material was dissolved in ethyl acetate, 5% palladium-on-carbon was added and the mixture was hydrogenated at room temperature with gaseous H$_2$ to remove the benzyl group, followed by a similar hydrogenation with 5% platinum-on-carbon to remove the phenyl groups. Freeze drying of the filtrate after removing the catalyst produced PAA-Gly in a yield of 84%.

EXAMPLE 2

In the manner of Example 1, D-alanine benzyl ester was converted to the corresponding PAA-D-Ala. The pure compound shows [α]$^{24}$ of +6.8° (c=1.1; DMF). The analogous PAA-L-Ala, made in the same fashion shows [α]$^{24}$ −2.6° (c=1.0; DMF).

EXAMPLE 3

In the manner of the preceding examples, the benzyl ester of β-alanine was converted to PAA-β-Ala which was obtained in an excellent overall yield.

EXAMPLE 4

In a slight modification of Example 1, the benzyl ester of glycylaspartic acid was condensed with an equimolar amount of P,P-dibenzyl-PAA. The subsequent hydrogenation with a palladium catalyst removed all benzyl groups simultaneously, producing PAA-Gly-Asp in excellent yield, [α]$^{25}$ −3.1° (c=1; H$_2$O).

EXAMPLE 5

In analogy to Example 1, PAA-D-Leu and PAA-L-Leu were prepared. Both were obtained in above 80% yield and showed [α]$^{24}$ rotations at +9.5° and −10.6°, respectively (c=1; DMF).

EXAMPLE 6

In the same manner, asparagine benzyl ester is used to produce PAA-Asn in good yield; [α]$^{24}$ +5.5° (c=1; H$_2$O).

EXAMPLE 7

The above compounds were tested for herpes DNA polymerase activity in the manner shown in Example 9 of U.S. Pat. No. 4,138,432. The assay, using fixed dilutions of the above compounds, produced the following results:

| Compound | % Inhibition at Drug Level | | |
|---|---|---|---|
| | 166 | 16.6 | 1.666 μg/ml |
| PAA-Na | 99 | 98 | 82 |
| Example 1 | 72 | 56 | 33 |
| Example 2 (D) | 87 | 68 | 19 |
| Example 2 (L) | 59 | | |
| Example 3 | 88 | 59 | 15 |
| Example 4 | 93 | 77 | 39 |

When variable solution concentrations were used, the results were as follows:

| Compound of | ID50 |
| --- | --- |
| Example 1 | 5.7 μg/ml |
| Example 2 (D-form) | 6.6 μg/ml |
| Example 3 | 10.6 μg/ml |
| Example 4 | 3.3 μg/ml |

EXAMPLE 8

In order to show the efficacy of the above aminoacid derivatives of PAA, the following procedure was used to determine the 50% survival rate in mice: Female, 20 g., CF mice, under light ether anaesthesia, had a 2-cm$^2$ area of their back plucked free of hair. Infectious HSV-2, strain MS (0.05 ml., $10^7$ TCIA$_{50}$ per ml.) was applied topically to the denuded skin. A 27-gauge sterile hypodermic needle was used to prick the surface of the skin beneath the drop. In untreated (control) mice, a small lesion developed in 3 to 5 days and the lesion extended across the denuded area in the following 3 to 4 days. At approximately day 10 the mice developed a flacid, posterior paralysis. Once paralyzed, death usually followed in 24 hours.

The new PAA analogs were applied as a 2% aqueous solution to the site 2 hours after the virus infection. Medication was applied twice daily for 5 consecutive days. Each application of the 2% solution delivered about 2 mg. of the compound. The observation period lasted 17 days. Ten mice were used for each compound. The Mann-Whitney "U" Test was used to statistically analyze the herpes infection in mice by making paired comparisons between infected, treated mice and infected untreated mice.

The Mann-Whitney "U" test [Siegal; Non-Parametric Statistics for the Behavioral Sciences; McGraw Hall, p. 116 (1956)] used to statistically analyze the herpes infection in mice made paired comparisons between treated and control groups. The groups showing a p value ≤ 0.10 from the virus control are active on a statistically significant basis. The results were as follows:

| Compound | P Value |
| --- | --- |
| PAA-L-Leu | 0.05 |
| PAA-Asp-NH2 | 0.1 |
| PAA-D-Leu | 0.05 |

As seen in the above tables, the new PAA-derivatives are very potent against herpes virus. The specific aminoacids described herein are unique in this respect as other aminoacid derivatives of PAA are far less potent and more toxic. For instance, the PAA-L-Asp (known as a chemotherapy test drug as PALA) has an ID$_{50}$ of 36 μg/ml and the value for PAA-Arg is 60 μg/ml. Also, the acute toxicity of the new compounds is between 1/10 to 1/100 the toxicity of other PAA aminoacids or PAA-Na.

It will be obvious to those skilled in the art that salts can readily be obtained from the above free acids. Particularly suitable for the medicinal application of the new drugs are the nontoxic cations in the terminal carboxylic acid group(s), e.g., Na, K, Ca which are preferred, although for certain topical applications, the corresponding Mg or Al salts can also be used.

The compounds of the present invention can be incorporated into a topical powder by simply combining them homogenously with talcum powder in a concentration of 1-5%. If desired, moisture absorbers, adhesive agents, perfumes and opacifying agents may be added. A typical formula contains 60% of talcum, 22% of kaolin, 16% of bentonite and 2% of the new compound.

Solid dosage forms can also be applied by means of a dressing, gauze or other cellulosic material soaked in a solution of the new compound, such as an ethanol solution. The solvent is then evaporated, leaving the dry material on the fabric which is then used as a dressing for the afflicted skin area.

A topical solution can easily and simply the made by dissolving the new compounds at a concentration of 1-2% in an alcohol, preferably 70-100% ethanol, although propanol or isopropanol can be used as well.

Topical creams can be prepared in the usual fashion whereby one of the new compounds is combined, at a concentration of 0.5-5.0%, with primary and secondary emulsifiers, thickeners, emollients, oleaginous material, humectants, preservatives and water containing, if desired, a stabilizer and/or a buffer. Similarly, lotions can be made by combining the new compound with the ingredients used in the above solution but containing also one or more preservatives and stabilizers.

Ointments are made with the ingredients listed above for creams and combined in the fashion known to those skilled in the art. Petrolatum is ordinarily used as the oleaginous base which may be combined with lanolin.

For more sophisticated formulations, the new antiherpes drug can be incorporated into an aerosol. A suitable aerosol is made by combining a 1-2% alcoholic solution of the new compound with one or more propellants. Without the propellant, the solution is most advantageously placed in a rigid or semirigid spray bottle from which the solution is atomized through a suitable orifice by squeezing the semirigid container or through a pump device.

We claim:

1. A compund of the formula

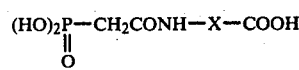

wherein X stands for >CHCH₃, —CH₂—, —CH₂CH₂—, >CHCH₂CH(CH₃)₂, >CHCH₂CONH₂ or

and the nontoxic salts thereof.

2. The compound of claim 1 wherein X is CH₂.
3. The compound of claim 1 wherein X is >CHCH₃.
4. The compound of claim 1 wherein X is —CH₂CH₂—.
5. The compound of claim 1 wherein X is

6. The compound of claim 1 wherein X is >CHCH₂CH(CH₃)₂.

7. The compound of claim 1 wherein X is >CHCH₂CONH₂.

8. A topical pharmaceutical composition for treating herpes virus infections in warm-blooded animals comprising a compound of the formula:

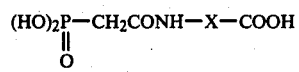

wherein X stands for >CHCH₃, —CH₂—, —CH₂CH₂—, >CHCH₂CH(CH₃)₂, >CHCH₂CONH₂ or

and the nontoxic salts thereof, together with a topically acceptable diluent.

9. The composition of claim 8 wherein X is —CH₂.
10. The composition of claim 8 wherein X is >CHCH₃.
11. The composition of claim 8 wherein X is —CH₂CH₂³¹.
12. The composition of claim 8 wherein X is

13. The composition of claim 8 wherein X is >CHCH₂CH(CH₃)₂.

14. The composition of claim 8 wherein X is >CHCH₂CONH₂.

15. A method for treating herpes simplex virus infection in a warm-blooded animal which comprises administering to an animal so infected, an effective amount to combat said virus of a composition containing a compound of the formula

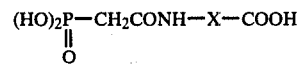

wherein X stands for >CHCH₃, —CH₂—, —CH₂CH₂—, >CHCH₂CH(CH₃)₂, >CHCH₂CONH₂ or

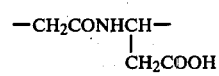

and the nontoxic salts thereof.

16. The method of claim 15 wherein X is —CH₂—.
17. The method of claim 11 wherein X is >CHCH₃.
18. The method of claim 11 wherein X is —CH₂CH₂.
19. The method of claim 11 wherein X is

20. The method of claim 15 wherein X is >CHCH₂CH(CH₃)₂.
21. The method of claim 15 wherein X is >CHCH₂CONH₂.

* * * * *